United States Patent [19]

Petersen

[11] Patent Number: 5,002,555
[45] Date of Patent: Mar. 26, 1991

[54] GALL-RESISTANT RIBBED SURGICAL SAW BLADE

[76] Inventor: Thomas D. Petersen, 9680 Alto Dr., La Mesa, Calif. 92041

[21] Appl. No.: 308,607

[22] Filed: Feb. 10, 1989

[51] Int. Cl.$^5$ .............................................. A61B 17/14
[52] U.S. Cl. ..................................... 606/176; 30/351; 83/835
[58] Field of Search ................. 606/177, 176, 178, 82; 30/166.3, 351, 355, 504, 502, 503, 503.5, 374, 348; 83/835, 847

[56] References Cited

U.S. PATENT DOCUMENTS

| | | | |
|---|---|---|---|
| 336,697 | 2/1886 | Clemson | 83/835 |
| 486,426 | 11/1892 | Brooks | 30/348 |
| 563,521 | 7/1896 | Walter | 30/166.3 |
| 1,929,838 | 10/1933 | Crane | 30/348 X |
| 2,958,943 | 11/1960 | Koe | 30/355 X |

*Primary Examiner*—Michael H. Thaler
*Attorney, Agent, or Firm*—H. Jay Spiegel

[57] ABSTRACT

The present invention relates to a gall-resistant ribbed surgical saw blade. The blade includes longitudinal ribs extending outwardly from the opposed faces thereof which combine to define a local blade thickness greater than the width of the lateral extension of the teeth thereof. The ribs are sized and configured to slidably engage a precision slot in a guide means designed to be used to guide the blade in cutting movements. The interaction between the ribs and the slot prevents engagement of the blade teeth with the slot while reducing the surface area of engagement of the blade with the slot to reduce friction.

8 Claims, 1 Drawing Sheet

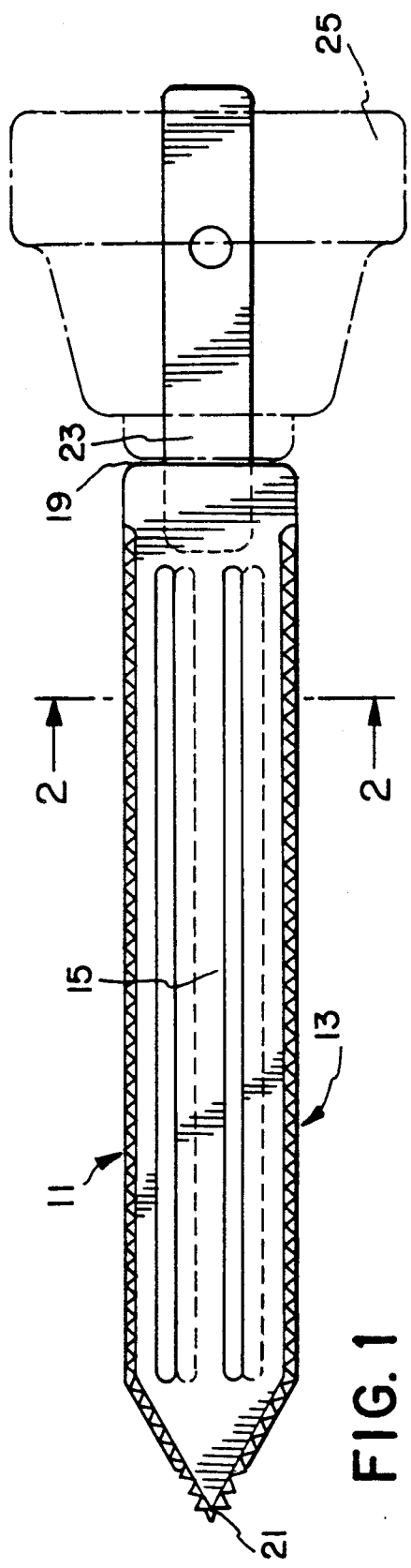
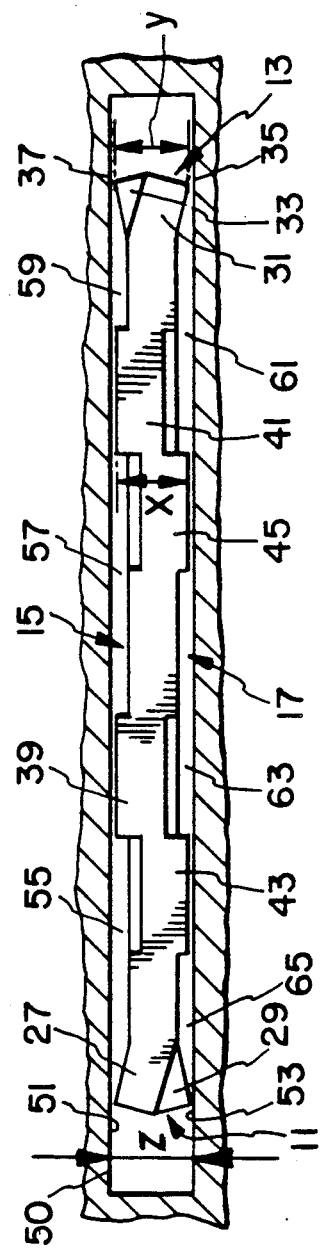
FIG. 1
FIG. 2

GALL-RESISTANT RIBBED SURGICAL SAW BLADE

BACKGROUND OF THE INVENTION

The present invention relates to a gall-resistant ribbed surgical saw blade. Orthopedic surgeons utilize saw blades of various shapes and configurations in the performance of surgical procedures. One such saw blade is known as a reciprocating saw blade and is designed to interact with a precision slot which guides the saw blade in reciprocating movements to cut bone tissue during the performance of surgery.

Customarily, a reciprocating surgical blade has a plurality of teeth on each of its two edges. These teeth are customarily provided in a set, that is, consecutive teeth are bent in alternate directions. As this set is provided on known surgical saw blades, the ends of the teeth extend upwardly and downwardly beyond the respective planes of the respective side faces of the blade. Thus, often, it is these ends of the teeth which guide the saw blade within the precision slot. Of course, inherently, this causes wear of the teeth quite prematurely and results in the surgeon having to change saw blades quite often during the surgical case.

Studies have been conducted on the effect on bone tissue of blades which have been galled for whatever reason. In article titled "Orthopedic Saw Blades A Case Study" by H.W. Wevers, et al, published in the Journal of Arthroplasty, Volume 2 No. 1, March 1987, this problem is discussed. The following is quoted from this article: "Because these blades are used primarily for total knee arthroplasty, it is probable that the damage occurred from direct contact of the cutting edges with metal templates or instruments used in the operation. This type of damage had a direct influence on the mechanical work needed to operate the saw." Later in the publication, the following is stated: "Excessive heat induces thermal damage to osteocytes and expands the zone of necrosis beyond that shown microscopically." Further, the following is stated: "Smooth, accurately cut surfaces are recognized as an important factor for bone ingrowth into porous-coated prostheses. Such clean bone cuts enhance prosthetic fit and setting, therefore promoting an even load bearing to the bone, and improved alignment of the prostheses or osteotomies." Finally, the following is stated: "Damage to blade cutting surfaces due to inadvertent contact with templates and instruments may be unavoidable with currently available techniques."

Further, a publication titled "Avoiding Thermal Damage to Bone: Machining Principals [SIC] Applied to Powered Bone Surgery a Literature Review", by Ray Umber, et al. further discusses the problems attendant in the prior art. The following is disclosed therein: "Thus, cutting with a dull tool, increases the amount of frictional heat generated, much of which is now located in the workpiece itself. With a dull tool not only is the surface of the workpiece increasing in temperature but also the cut is no longer clean."

A further problem with prior art saw blades is also set forth in this publication. In particular, prior art saw blades are so designed that it is difficult to provide water to the site of the operation for cooling purposes and to remove bone chips which are generated during sawing. Due to present saw blade design, "coolant can not reach the dissection site". "It is, therefore, important to allow chip relief and to allow a cooling fluid to reach the dissection site and the dissecting tool. Proper attention to the technique will allow chip relief and the introduction of cooling irrigation, resulting in healthy, living bone which will heal readily."

Thus, a need has developed in the prior art for a surgical saw blade which will not only be more durable in use, but which will reduce heat generation adjacent bone tissue while also allowing access of cooling and flushing water to the surgical site.

The following prior art is known to applicant:

U.S. Pat. Nos.

D 30,478 to Earle
864,812 to Thullier
2,670,939 to Harp
3,517,670 to Speelman
4,036,236 to Rhodes, Jr.

Earle discloses a grass cutting blade having a single rib extending outwardly from one face thereof. Of course, this is different from the teachings of the present invention in that the present invention contemplates ribs on opposed faces of a blade having teeth formed in a set with the ribs guiding the blade in a precision slot.

Thullier discloses a knife and other cutting blade in several embodiments. As the cross-sections demonstrate, each of the blades disclosed in this patent have differing cross-sectional thicknesses at different areas along the lengths thereof which would make it impossible to use these blades in conjunction with a precision slot. Furthermore, none of the embodiments of Thullier teach the use of teeth provided in a set configuration.

Harp discloses a mixing paddle having a plurality of rib-like structures thereon which appear to be of differing thicknesses as best seen in FIG. 4. Thus, Harp is quite distinct from the teachings of the present invention as failing to disclose a cutting blade and as not being designed for use in conjunction with a precision slot, among other reasons.

Speelman discloses a blood-letting lancet having two longitudinal ribs extending from one face thereof and a point at one or both ends thereof. The present invention is distinct from the teachings of Speelman as including ribs on opposed faces of an elongated blade having teeth on opposed sides thereof, which teeth are formed in a set configuration.

Finally, Rhodes teaches the concept of a surgical saw blade having teeth on one side thereof and a single elongated longitudinal rib extending outwardly from one face thereof. The lack of a plurality of ribs on opposed faces of the Rhodes, Jr. blade would inherently allow pivoting of the blade from side to side as it moves in a precision slot thus inherently damaging the tooth set.

Concerning the prior art discussed above, while ribs are disclosed in these patents in conjunction with elongated blades, the ribs are disclosed only for strengthening purposes. While the ribs of the present invention inherently strengthen the elongated blade, their main purpose is to provide guidance of the blade within a precision slot. This is different from the teachings of the prior art.

SUMMARY OF THE INVENTION

The present invention relates to a gall-resistant ribbed surgical saw blade. The present invention includes the following interrelated aspects and features:

(a) In a first aspect, the inventive saw blade consists of an elongated blade having two opposed sides, a distal end, a proximal end and two opposed faces.

(b) Each of the opposed sides of the elongated blade has a plurality of teeth formed thereon extending from adjacent the proximal end to adjacent the distal end thereof. In each case, these teeth are formed in a set whereby adjacent teeth are formed or bent in opposed directions whereby the ends of the teeth extend outwardly beyond the respective planes defining the majority of the opposed faces thereof.

(c) In the preferred embodiment of the present invention, each of the opposed faces has a plurality of longitudinally extending ribs extending outwardly from each respective face. The ribs extend outwardly from the respective faces of the blade a sufficient distance so that the thickness of the elongated blade from the outward termination of a rib on one face to the outward termination of a rib on the opposed face is greater than the width of the outwardmost extensions of the ends of the respective teeth of the blade as they are formed in the set as defined and described hereinabove. In this way, when the elongated blade is guided in a precision slot, the teeth of the blade will not engage the inner surfaces of the guide slot.

(d) The above described precision slot includes a guide slot which is sized and configured to slidably receive an elongated surgical saw blade having the above described ribs formed thereon in a sliding fit in engagement with the ribs only. In this way, the surface area of engagement between the blade and the slot is reduced thereby reducing frictional forces with spaces between the respective ribs allowing water flow through the precision slot with the elongated blade therein thereby enhancing the flushing and cooling effects of the water.

Accordingly, it is a first object of the present invention to provide an improved gall-resistant ribbed surgical saw blade.

It is a further object of the present invention to provide such an improved surgical saw blade with a plurality of elongated ribs designed to guide the saw blade in a precision slot while spacing the teeth from engagement with the slot.

It is a yet further object of the present invention to provide such a surgical saw blade whereby the use of ribs enhances the flow of cooling and flushing water to the surgical site.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a side view of the preferred embodiment of saw blade of the present invention.

FIG. 2 shows a cross-sectional view along the line 2—2 of FIG. 1.

SPECIFIC DESCRIPTION OF THE PREFERRED EMBODIMENT

With reference to the Figures, the inventive blade is generally designated by the reference numeral 10 and is seen to include opposed sides 11 and 13, opposed faces 15 and 17, a proximal end 19 and a distal end 21.

The proximal end 19 has a shank 23 designed to be used to couple the saw blade 10 to the chuck 25 of a reciprocating saw device (not shown). As is well known by those skilled in art, the reciprocating saw device includes a motor whether electrically, hydraulically or pneumatically actuated, which causes controllable reciprocation of the blade 10.

With particular reference to FIG. 2, it is seen that each side 11, 13 of the plate 10 has a plurality of teeth thereon with two teeth being shown on each side of FIG. 2. The two teeth on the side 11 of the blade 10 are designated by the reference numerals 27 and 29 whereas the two teeth on the side 13 are designated by the reference numerals 31 and 33. As is seen in FIG. 2, the respective adjacent teeth are formed in a set whereby, for example, the tooth 27 is bent upwardly and the tooth 29 is bent downwardly. Similarly, the tooth 31 is bent downwardly whereas the tooth 33 is bent upwardly.

In considering the teeth 31 and 33, for example, the tooth 31 has an outwardmost point 35 while the tooth 33 has an outwardmost point 37.

As best seen in FIG. 2, each face 15, 17 of the blade 10 has a plurality of ribs extending outwardly therefrom. Thus, the face 15 has ribs 39 and 41 extending outwardly therefrom whereas the face 17 has ribs 43 and 45 extending outwardly therefrom.

In an important aspect of the present invention, the thickness of the blade 10 as defined between the outermost extension of the ribs 39 and 43 on the one hand and the ribs 41 and 45 on the other hand is specifically designed to be slightly greater than the thickness of the blade 10 as defined by the distance from the point 35 of the tooth 31 and the point 37 of the tooth 33 as well as the corresponding points on the teeth 27 and 29. FIG. 2 shows a schematic representation of the configuration of a slot 50 termed a precision slot, through which the blade 10 may be guided. The above described relationship between the thickness of the blade 10 at the ribs and the thickness of the blade at the teeth may be best understood by viewing the fact that as the blade 10 is guided within the precision slot 50, the outward faces of the ribs 39, 41, 43, and 45 slidingly engage the inner faces 51, 53 at the slot 50 while the teeth of the blade 10 never engage the faces 51 and 53 of the precision slot 50. Thus, it should be understood that when the blade 10 is guided within the precision slot 50, the elimination of engagement of the teeth with the inner surfaces thereof prevents premature galling of the teeth which would occur through such engagement.

In a further aspect, it should be understood from FIG. 2 that the inclusion of the ribs 39, 41, 43 and 45 on the blade 10 causes the defining of a plurality of passages 55, 57, 59, 61, 63 and 65 between the outer faces of the blade 10 and the inner walls 51 and 53 of the precision slot. These passages allow water to flow through the precision slot 50 while the blade 10 is inserted therein and guided thereby to allow cooling and flushing of the surgical site during sawing operations. This is a distinct advantage over the prior art.

The ribs 39, 41, 43 and 45 may be formed by any suitable means. For example, the blade may be initially manufactured as a flat blade and the ribs may be formed thereon through a stamping operation. Alternatively, the blade may be cast with the blades formed as a part of the casting.

Furthermore, the blade itself may be made of any suitable metallic material. One material which has been found to be effective for use in a surgical saw blade is known in the art as 410 stainless steel.

As seen in FIG. 2, the distance between the outer surfaces of the ribs 39 and 43 is designated by the reference letter x whereas the distance between the point 35 and 37 of the respective teeth 31 and 33 is designated by the reference letter y. In the preferred embodiment of the present invention, the precision slot has a thickness z from face 51 to face 53 of 0.040 inches with dimension x preferably being 0.038 inches and dimension y preferably being 0.036 inches. Thus, in this preferred configuration, which is to be considered merely exemplary, the points 33 and 35 of the teeth 31 and 33 are respectively spaced from the faces 53 and 51 of the precision slot 50 by 0.01 inches each.

Accordingly, an invention has been disclosed in terms of a preferred embodiment which fulfills each and every one of the objects of the invention set forth hereinabove and provides a reciprocating saw blade of increased strength and life and which reduces bone tissue damage in use.

Of course, various changes, modifications and alterations in the teachings of the present invention may be contemplated by those skilled in the art without departing from the intended spirit and scope of the present invention. As such, it is intended that the present invention only be limited by the terms of the appended claims.

I claim:

1. A surgical saw blade for use in conjunction with a slot having parallel guiding faces, comprising:
   (a) an elongated body having first and second faces lying in substantially parallel planes and extending substantially the entire length of said elongated body, one of said first and second faces having at least one longitudinal rib protruding outwardly therefrom, the other of said first and second faces having at least two longitudinal ribs protruding outwardly therefrom and laterally staggered with respect to said at least one longitudinal rib;
   (b) said blade having two sides defining the lateral extent of said first and second faces, at least one of said sides having a plurality of teeth thereon, respective adjacent pairs of said teeth defining a first thickness in a direction perpendicular to said substantially parallel planes;
   (c) said first thickness being less than a second thickness defined by the outward extent of opposed said ribs whereby when said blade is inserted in a slot, parallel guiding faces thereof solely engage said ribs and said teeth are maintained spaced therefrom.

2. The invention of claim 1, wherein said one of said first and second faces has at least two ribs extending outwardly therefrom.

3. The invention of claim 1, wherein said teeth are formed in a set.

4. The invention of claim 3, wherein each of said sides has a plurality of teeth thereon.

5. The invention of claim 1, wherein said ribs have flat terminating faces, said ribs being formed by stamping said blade.

6. The invention of claim 1, wherein said ribs have flat terminating faces and said blade is cast with said ribs formed during casting.

7. The invention of claim 1, wherein said blade is made of stainless steel.

8. In combination, a slot having parallel guiding faces and a surgical saw blade slidably insertable in said slot, said surgical saw blade comprising:
   (a) an elongated body having first and second faces lying in substantially parallel planes and extending substantially the entire length of said elongated body, one of said first and second faces having at least one longitudinal rib protruding outwardly therefrom, the other of said first and second faces having at least two longitudinal ribs protruding outwardly therefrom and laterally staggered with respect to said at least one longitudinal rib;
   (b) said blade having two sides defining the lateral extent of said first and second faces, at least one of said sides having a plurality of teeth thereon, respective adjacent pairs of said teeth defining a first thickness in a direction perpendicular to said substantially parallel planes;
   (c) said first thickness being less than a second thickness defined by the outward extent of opposed said ribs whereby when said blade is inserted in said slot, said parallel guiding faces thereof solely engage said ribs and said teeth are maintained spaced therefrom.

* * * * *